US00PP33184P2

(12) United States Plant Patent
Kievit

(10) Patent No.: US PP33,184 P2
(45) Date of Patent: Jun. 22, 2021

(54) ***NEPETA* PLANT NAMED 'BALPURRINK'**

(50) Latin Name: ***Nepeta* hybrid**
Varietal Denomination: Balpurrink

(71) Applicant: Ball Horticultural Company, West Chicago, IL (US)

(72) Inventor: Christa Kievit, Hem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/005,624

(22) Filed: Aug. 28, 2020

(51) Int. Cl.
*A01H 5/02* (2018.01)
*A01H 6/50* (2018.01)

(52) U.S. Cl.
USPC ..... Plt./263.1
CPC ..... *A01H 6/50* (2018.05)

(58) Field of Classification Search
USPC ..... Plt./263.1
CPC ..... A01H 5/02; A01H 5/12
See application file for complete search history.

(56) References Cited

PUBLICATIONS http://hardyplugs.com/eme.htm; Jun. 30, 2020; 2 pages.*

* cited by examiner

*Primary Examiner* — Kent L Bell
(74) *Attorney, Agent, or Firm* — Audrey Charles

(57) ABSTRACT

A new and distinct cultivar of *Nepeta* plant named 'Balpurrink', characterized by its pale purple-colored flowers, medium green-colored foliage, and moderately vigorous, upright-mounded growth habit, is disclosed.

1 Drawing Sheet

Latin name of genus and species of plant claimed: *Nepeta* hybrid.

Variety denomination: 'Balpurrink'.

BACKGROUND OF THE INVENTION

The present invention relates to a new and distinct cultivar of *Nepeta* plant botanically known as *Nepeta* hybrid and hereinafter referred to by the cultivar name 'Balpurrink'.

The new cultivar originated in a controlled breeding program in Hem, the Netherlands during August 2015. The objective of the breeding program was the development of *Nepeta* cultivars having a long flowering season, large inflorescences, and an upright-mounded growth habit.

The new *Nepeta* cultivar is the result of self-pollination of the proprietary *Nepeta* hybrid breeding selection coded C10-1, not patented, characterized by its medium violet-blue colored flowers, medium grey-green colored foliage, and moderately vigorous, upright growth habit. The new cultivar was selected as a single flowering plant within the progeny of the above stated self-pollination during July 2016 in a controlled environment in Hem, the Netherlands.

Asexual reproduction of the new cultivar by terminal stem cuttings since July 2016 in Hem, the Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balpurrink' as a new and distinct cultivar of *Nepeta* plant:

1. Pale purple-colored flowers;
2. Medium green-colored foliage; and
3. Moderately vigorous, upright-mounded growth habit.

Plants of the new cultivar differ from plants of the parent primarily in having pale purple-colored flowers, larger inflorescences, and a more mounded growth habit.

Of the many commercially available *Nepeta* cultivars, the most similar in comparison to the new cultivar is 'Walker's Low', not patented. However, in side-by-side comparison, plants of the new cultivar differ from plants of 'Walker's Low' in at least the following characteristics:

1. Plants of the new cultivar are shorter than plants of 'Walker's Low';
2. Plants of the new cultivar have green-colored foliage which is different from the grey-green colored foliage of plants of 'Walker's Low';
3. Plants of the new cultivar have pale purple-colored flowers which is different from the violet-blue colored flowers of plants of 'Walker's Low'; and
4. Plants of the new cultivar have a longer bloom period than plants of 'Walker's Low'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balpurrink'. The plants were approximately 14 weeks old. The plants were grown in 1.72-gallon containers for approximately 7 weeks in an outdoor nursery in West Chicago, Ill. Plants were given two pinches prior to transplant.

DETAILED BOTANICAL DESCRIPTION

Figure 1:
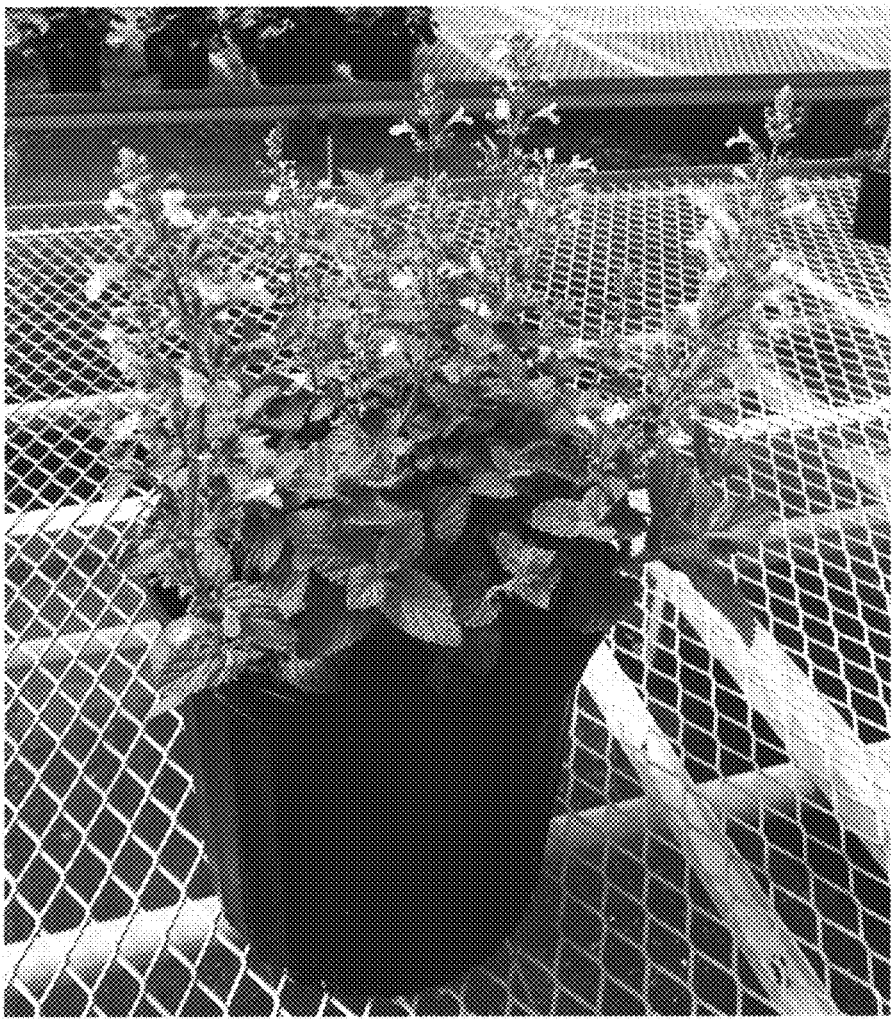
FIG. 1 illustrates a side view of the overall growth and flowering habit of 'Balpurrink'.
Figure 2:
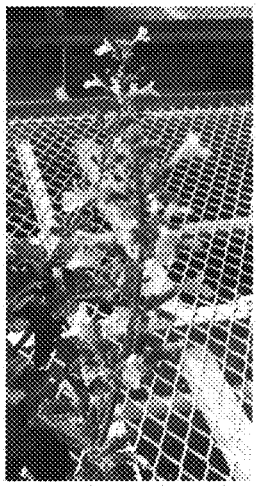
FIG. 2 illustrates a close-up view of an inflorescence of 'Balpurrink'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2020 under natural light conditions in Naperville, Ill.

The following descriptions and measurements describe approximately 14 weeks old plants produced from cuttings from stock plants and grown under conditions comparable to those used in commercial practice. The plants were grown in 1.72-gallon containers for approximately 7 weeks in an outdoor nursery in West Chicago, Ill. Plants were given two pinches prior to transplant. Prior to transplant plants were grown in liners in a poly-covered greenhouse in West Chicago, Ill. Greenhouse temperatures ranged from an average high of 69.3° F. (20.7° C.) to an average low of 63.6° F. (17.6° C.), and supplemental lighting was provided daily for five hours during short days. Measurements and numerical values represent averages of typical plants.

Botanical classification: *Nepeta* hybrid 'Balpurrink'.

Parentage:

*Female and male parents*.—Proprietary *Nepeta* hybrid breeding selection coded C10-1, not patented.

Propagation:

*Type cutting*.—Terminal stem.

*Time to initiate roots*.—Approximately 10 to 12 days.

*Time to produce a rooted cutting*.—Approximately 5 to 6 weeks.

*Root description*.—Fine to medium, fibrous.

*Rooting habit*.—Freely branching.

Plant description:

*Commercial crop time*.—Approximately 9 to 11 weeks from a rooted cutting to finish in a 15 cm pot.

*Growth habit and general appearance*.—Herbaceous perennial; moderately vigorous, upright-mounded growth habit.

*Hardiness*.—USDA Zone 4 (−30° F. to −20° F./−34.4° C. to −28.9° C.).

*Size*.—Height from soil level to top of plant plane: Approximately 27.0 cm. Width: Approximately 36.0 cm.

*Branching habit*.—Freely branching slightly decumbent, pinching enhances lateral branching. Quantity of branches per plant: Approximately 5 main branches, each having up to 8 axillary branches.

*Lateral branch*.—Shape: Square in cross section. Strength: Strong, flexible. Length to base of peduncle: Approximately 11.0 cm Diameter: Approximately 3.0 mm. Length of central internode: Approximately 2.3 cm. Texture: Densely pubescent. Color of young and mature stem: 146C.

Foliage description:

*General description*.—Quantity of leaves per branch: Approximately 10 to 14. Fragrance: Moderate minty. Form: Simple. Arrangement: Opposite.

*Leaves*.—Aspect: Petiole at acute angle to stem with blade perpendicular. Shape: Ovate. Margin: Serrate with slightly rounded teeth. Apex: Broadly acute. Base: Cordate. Venation pattern: Pinnate. Length of mature leaf: Approximately 3.8 cm. Width of mature leaf: Approximately 2.8 cm. Texture of upper and lower surfaces: Densely pubescent. Color of upper surface of young and mature foliage: Closest to 137A to 137B with venation of 146C. Color of lower surface of young and mature foliage: Closest to 147B with venation of 147C.

*Petiole*.—Length: Approximately 1.2 cm. Diameter: Approximately 1.0 mm. Texture: Densely pubescent. Color: 146C.

Flowering description:

*Flowering habit*.—'Balpurrink' is a long-day facultative, freely flowering blooming from spring through summer under outdoor growing conditions.

*Lastingness of individual floret*.—Approximately 6 to 7 days.

Inflorescence description:

*General description*.—Type: Terminal, dense, multiflowered head-like cyme. Quantity of open inflorescences per plant: Approximately 12. Fragrance: Moderate minty. Length or height of inflorescence: Approximately 11.0 cm to 18.0 cm. Width of inflorescence: Approximately 4.0 cm. Quantity of fully open flowers per inflorescence: Approximately 4 to 19.

*Peduncle*.—Strength: Strong. Aspect: Erect. Length: Approximately 4.0 cm. Diameter: Approximately 2.0 mm to 3.0 mm. Texture: Densely pubescent. Color: 146C.

Flower description:

*Type*.—Single, zygomorphic.

*Bud just before opening*.—Shape: Clavate. Length: Approximately 1.5 cm. Diameter: Approximately 4.0 mm. Texture: Densely pubescent with a mixture of glandular and nonglandular hairs. Gland color: Colorless, transparent. Color: 69B.

*Corolla*.—Shape: Bilabiate with a bell-shaped tube, upper lip of two lobes and lower lip having three lobes. Aspect: Facing upward and outward. Width: Approximately 5.0 mm. Length: Approximately 8.0 mm. Depth: Approximately 1.8 cm.

*Upper lip lobes*.—Shape: Oblong. Margin: Entire. Apex: Rounded. Length from throat: Approximately 3.0 mm. Width: Approximately 2.0 mm. Texture of upper (inner) surface: Glabrous. Texture of lower (outer) surface: Densely pubescent with a mixture of glandular and nonglandular hairs. Gland color: Colorless, transparent. Color of upper (inner) surface when first and fully open: 69C. Color of lower (outer) surface when first and fully open: 69D.

*Lower lip, lateral lobes*.—Shape: Orbicular. Margin: Entire. Apex: Rounded. Length from throat: Approximately 2.0 mm. Width: Approximately 2.0 mm. Texture of upper (inner) surface: Glabrous. Texture of lower (outer) surface: Moderately pubescent with a mixture of glandular and nonglandular hairs. Gland color: Colorless, transparent. Color of upper (inner) surface when first and fully open: 69C. Color of lower (outer) surface when first and fully open: 69D.

*Lower lip, central lobe*.—Shape: Cup-like. Margin: Crenate. Apex: Rounded. Length from throat: Approximately 6.0 mm. Width: Approximately 4.0 mm. Texture of upper (inner) surface: Densely pubescent at center at throat opening. Texture of lower (outer) surface: Densely pubescent in center with a mixture of glandular and nonglandular hairs. Gland color: Colorless, transparent. Color of upper (inner) surface when first and fully open: 69C with NN155D in center and spots of 83D. Color of lower (outer) surface when first and fully open: 69D.

*Corolla tube*.—Length: Approximately 1.2 cm. Width at opening: Approximately 4.0 mm. Width at base: 1.0 mm. Texture of inner surface: Glabrous. Texture of outer surface: Densely pubescent with a mixture of glandular and nonglandular hairs. Gland color: Colorless, transparent. Color of inner surface: NN155D with spots of 83C to 83D. Color of outer surface: 69D.

*Calyx*.—Shape: Tubular with 5 tips. Length: Approximately 8.0 mm. Diameter: Approximately 2.0 mm.

*Sepals*.—Quantity per flower: 5. Margin: Entire. Apex: Acute. Base: Fused. Length: Approximately 8.0 mm. Width: Approximately 1.0 mm. Texture of inner surface: Glabrous. Texture of outer surface: Densely pubescent with a mixture of glandular and nonglandular hairs. Gland color: Colorless, transparent. Color of inner surface: 146D. Color of outer surface: 146D occasionally lightly tinted with N186A.

*Pedicel*.—Strength: Strong, flexible. Aspect: At an acute angle. Length: Approximately 1.0 mm to 2.0 mm. Diameter: Approximately 1.0 mm. Texture: Densely pubescent. Color: 146D.

*Reproductive organs*.—Androecium: Stamen quantity: 4 per flower. Stamen length: Approximately 1.6 cm. Filament length of free portion: Approximately 4.0 mm to 5.0 mm. Filament color: 69C. Anther shape: Divergent, opening by a common slit. Anther length: Approximately 1.0 mm. Anther color: N80A. Pollen amount: Abundant. Pollen color: NN155D. Gynoecium: Pistil quantity: 1 per flower. Pistil length: Approximately 1.3 cm. Stigma shape: Bifurcate. Stigma length: Approximately 1.0 mm. Stigma color: N80B. Style length: Approximately 1.1 cm. Style color: NN155D with an overlay of N8OB near stigma. Ovary length: Approximately 1.0 mm. Ovary color: N144D.

Seed and fruit production: Neither seed nor fruit production has been observed.

Disease and pest resistance: Resistance to pathogens and pests common to *Nepeta* has not been observed.

What is claimed is:

1. A new and distinct cultivar of *Nepeta* plant named 'Balpurrink', substantially as herein illustrated and described.

* * * * *